(12) United States Patent
Wong et al.

(10) Patent No.: US 8,481,571 B2
(45) Date of Patent: Jul. 9, 2013

(54) ANTI-CORONAVIRUS COMPOUNDS

(75) Inventors: Chi-Huey Wong, Rancho Santa Fe, CA (US); Chung-Yi Wu, Hsinchu County (TW); Jia-Tsrong Jan, Taipei (TW)

(73) Assignee: Academia Sinica, Taipei (TW)

( * ) Notice: Subject to any disclaimer, the term of this patent is extended or adjusted under 35 U.S.C. 154(b) by 1796 days.

(21) Appl. No.: 11/121,314

(22) Filed: May 3, 2005

(65) Prior Publication Data

US 2006/0160866 A1 Jul. 20, 2006

Related U.S. Application Data

(60) Provisional application No. 60/568,080, filed on May 4, 2004.

(51) Int. Cl.
*A61K 31/44* (2006.01)
*A61K 31/40* (2006.01)
*A61K 31/165* (2006.01)
*A61K 31/325* (2006.01)

(52) U.S. Cl.
USPC ............ 514/357; 514/485; 514/563; 514/616

(58) Field of Classification Search
USPC .......................... 514/438, 357, 485, 563, 616
See application file for complete search history.

(56) References Cited

U.S. PATENT DOCUMENTS

| | | | |
|---|---|---|---|
| 5,019,495 A | 5/1991 | Shanbrom | |
| 5,142,056 A | 8/1992 | Kempe et al. | |
| 5,294,720 A * | 3/1994 | Jadhav et al. | 546/265 |
| 6,803,466 B1 | 10/2004 | Lee et al. | 546/146 |

FOREIGN PATENT DOCUMENTS

| JP | 3-128335 | 5/1991 |
|---|---|---|
| JP | 7-502970 | 3/1995 |

OTHER PUBLICATIONS

Buhler, Bernd, Viral Evolution in Response to the Broad-Based Reroviral Protease Inhibitor TL-3, Oct. 2001, Journal of Virology, vol. 75, Issue 19, pp. 9502-9508.*
Chan K.S., Treatment of Severe Acute Respiratory Syndrome with Lopinavir/Ritonavir: A multicentre retrospective matched cohort study, Dec. 2003, Hong Kong Journal of Medicine, vol. 9, Issue 6, pp. 399-406.*
Vastag, Brian, Old Drugs for a New Bug, Oct. 1, 2003, JAMA, vol. 290, Issue 13, pp. 1695-1696.*
Falsey, AR, Rhinovirus and Coronavirus Infection-Associated Hospitalizations Among Older Adults, May 2002, Journal of Infectious Diseases, vol. 185, PubMed Abstract, 1-2.*
Lee et al., "Development of a New Type of Protease Inhibitors, Efficacious Against FIV and HIV Variants", J. Am. Chem. Soc. 121:1145-1155, 1999.
Bioorganic & Medicinal Chemistry, 2003, 11 (22), p. 4719-4727.
Bioorganic & Medicinal Chemistry, 2001, 9 (5), p. 1185-1195.
Journal of Medicinal Chemistry, 1998, 41 (4), p. 602-617.
Bioorganic & Medicinal Chemistry Letters, 1994, 4 (2), p. 2851-2856.

* cited by examiner

*Primary Examiner* — Mina Haghighatian
*Assistant Examiner* — Andriae M Holt
(74) *Attorney, Agent, or Firm* — Fish & Richardson P.C.

(57) ABSTRACT

A method of treating coronavirus infection. The method includes administering to a subject suffering from or being at risk of suffering from such infection an effective amount of a compound of formula (I). Each variable in this formula is defined in the specification.

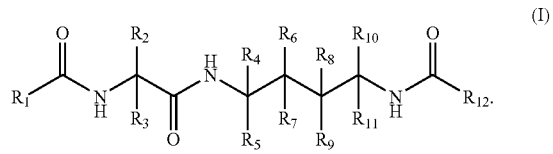

(I)

12 Claims, No Drawings

ANTI-CORONAVIRUS COMPOUNDS

CROSS REFERENCE TO RELATED APPLICATION

Under 35 U.S.C. §119, this application claims priority to U.S. Provisional Application Ser. No. 60/568,080, filed May 4, 2004, the contents of which are incorporated herein by reference.

BACKGROUND

Coronavirus is the cause of many common colds in humans. Recently, infection in humans with a new coronavirus led to a worldwide outbreak of an acute respiratory disease, i.e., severe acute respiratory syndrome. See, e.g., Ksiazek et al., *N. Engl. J. Med.*, 2004, 348: 1953-1966. The first severe acute respiratory syndrome case was identified in Guangdong, China in November, 2002. The disease later spread to more than 25 countries. By Jul. 31, 2003, about 8,100 severe acute respiratory syndrome cases and about 800 severe acute respiratory syndrome-related deaths were reported around the world.

Various drugs have been investigated for use in treating severe acute respiratory syndrome. They include ribavirin, corticosteroids, Kaletra, glycyrrhizin, and certain human interferons. See, e.g., Peris et al., *Lancet*, 2003, 361:1319; Cinatl et al., *Lancet*, 2003, 361:2045; and Cinatl et al., *Lancet*, 2003, 362:293. However, these drugs require high dosages to exert efficacy. Thus, there exists a need to identify compounds that can more effectively treat severe acute respiratory syndrome.

SUMMARY

This invention is based on an unexpected discovery that certain compounds are effective in treating an infection with a coronavirus (e.g., a severe acute respiratory syndrome virus).

In one aspect, this inventions features a method for treating a viral infection. The method includes administering to a subject (e.g., a mammal) suffering from or being at risk of suffering from an infection with a coronavirus (e.g., a severe acute respiratory syndrome virus) an effective amount of a compound of formula (I) or a salt thereof:

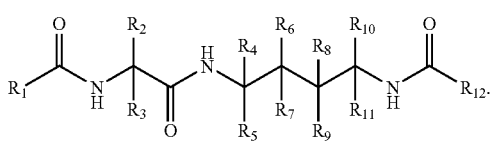

In this formula, $R_1$ is H, $C_1$-$C_{10}$ alkyl, $C_3$-$C_{20}$ cycloalkyl, $C_3$-$C_{20}$ heterocycloalkyl, heteroaryl, aryl, or $OR_a$; each of $R_2$, $R_3$, $R_4$ and $R_{10}$, independently, is H, $C_1$-$C_{10}$ alkyl, $C_3$-$C_{20}$ cycloalkyl, $C_3$-$C_{20}$ heterocycloalkyl, heteroaryl, or aryl; each of $R_5$ and $R_{11}$, independently, is alkyl substituted with aryl; each of $R_6$, $R_7$, $R_8$, and $R_9$, independently, is H, $C_1$-$C_{10}$ alkyl, $C_3$-$C_{20}$ cycloalkyl, $C_3$-$C_{20}$ heterocycloalkyl, heteroaryl, aryl, or $OR_b$; and $R_{12}$ is $C_1$-$C_{10}$ alkyl substituted with $OR_c$, NHC(O)$R_c$, or NHC(O)$OR_c$; in which each of $R_a$, $R_b$, and $R_c$, independently, is H, $C_1$-$C_{10}$ alkyl, $C_3$-$C_{20}$ cycloalkyl, $C_3$-$C_{20}$ heterocycloalkyl, heteroaryl, or aryl.

Note that one can administer a compound of formula (I) to a subject suffering from or being at risk of suffering from an infection with both a coronavirus (e.g., a severe acute respiratory syndrome virus) and a human or feline immunodeficiency virus. See, e.g., U.S. Pat. No. 6,803,466 and Lee et al., *J. Am. Chem. Soc.*, 1999, 121:1145-1155.

Referring to formula (I), a subset of compounds described above are those in which $R_1$ is $C_1$-$C_{10}$ alkyl, $C_3$-$C_{20}$ heterocycloalkyl, heteroaryl, aryl, or $OR_a$; each of $R_2$, $R_3$, $R_4$ and $R_{10}$, independently, is H or $C_1$-$C_{10}$ alkyl; and each of $R_6$, $R_7$, $R_8$, and $R_9$, independently, is H or $OR_b$. In these compounds, $R_1$ can be $C_1$-$C_{10}$ alkyl substituted with $C_3$-$C_{20}$ cycloalkyl, $C_3$-$C_{20}$ heterocycloalkyl, heteroaryl, aryl, OR, SR, or NHC(O)OR; R being H, $C_1$-$C_{10}$ alkyl, $C_3$-$C_{20}$ cycloalkyl, $C_3$-$C_{20}$ heterocycloalkyl, heteroaryl, or aryl; $R_2$ can be isopropyl; $R_5$ and $R_{11}$, can be alkyl substituted with phenyl; and each of $R_6$, $R_7$, $R_8$, and $R_9$, independently, can be H or OH.

The term "alkyl" refers to a saturated or unsaturated, linear or branched hydrocarbon moiety, such as —$CH_3$, —$CH_2$—$CH$=$CH_2$, or branched —$C_3H_7$. The term "cycloalkyl" refers to a saturated or unsaturated, non-aromatic cyclic hydrocarbon moiety, such as cyclohexyl or cyclohexen-3-yl. The term "heterocycloalkyl" refers to a saturated or unsaturated, non-aromatic cyclic moiety having at least one ring heteroatom (e.g., N, O, or S), such as 4-tetrahydropyranyl or 4-pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl, and indolyl.

Alkyl, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_8$ cycloalkyl, $C_5$-$C_8$ cycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halogen, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. Possible substituents on alkyl include all of the above-recited substituents except $C_1$-$C_{10}$ alkyl, $C_2$-$C_{10}$ alkenyl, and $C_2$-$C_{10}$ alkynyl. Cycloalkyl, heterocycloalkyl, aryl, and heteroaryl can also be fused with each other.

The term "treating" or "treatment" mentioned herein refers to administering one or more of the drug compounds described herein to a subject, who has an infection with a coronavirus, and possibly, also a human or feline immunodeficiency virus, a symptom of such an infection, or a predisposition toward such an infection, with the purpose to confer a therapeutic effect, e.g., to relieve, alter, affect, or ameliorate the viral infection, the symptom of it, or the predisposition toward it. Such a subject can be identified by a health care professional based on results from any suitable diagnostic method. "An effective amount" refers to the amount of the compound(s) required to confer a therapeutic effect on a treated subject or confer an inhibitory effect on a viral protease.

In another aspect, this invention features a packaged product including a container, a compound of formula (I), and a legend associated with the container and indicating administration of the compound for treating an infection with a coronavirus, such as a severe acute respiratory syndrome virus. The legend can also indicate administration of the compound for treating an infection with a human or feline immunodeficiency virus.

In still another aspect, this invention features a method for inhibiting a viral protease. The method includes contacting a coronavirus protease (such as a severe acute respiratory syndrome virus protease) with an effective amount of a compound of formula (I). The method can further includes contacting the compound with a human or feline immunodeficiency virus protease. See, e.g., U.S. Pat. No. 6,803,466 and Lee et al., J. Am. Chem. Soc., 1999, 121:1145-1155.

In still another aspect, this invention features the compounds of formula (I) or a salt thereof. Referring to this formula, the same groups as those described above are assigned to each variable except that $R_1$ is H, $C_3$-$C_{20}$ cycloalkyl, $C_3$-$C_{20}$ heterocycloalkyl, heteroaryl, aryl, $OR_a$, or $C_1$-$C_{10}$ alkyl substituted with $C_3$-$C_{20}$ cycloalkyl, $C_3$-$C_{20}$ heterocycloalkyl, heteroaryl, aryl, $OR_a$, or $SR_a$. A subset of the just-described compounds are those in which $R_1$ is $C_3$-$C_{20}$ heterocycloalkyl, heteroaryl, aryl, $OR_a$, or $C_1$-$C_{10}$ alkyl substituted with $C_3$-$C_{20}$ heterocycloalkyl, aryl, $OR_a$, or $SR_a$; each of $R_2$, $R_3$, $R_4$ and $R_{10}$, independently, is H or $C_1$-$C_{10}$ alkyl; and each of $R_6$, $R_7$, $R_8$, and $R_9$, independently, is H or $OR_b$.

In still another aspect, this invention features a method for treating an infection with a coronavirus by administering to a subject in need thereof an effective amount of a compound of formula (II) or a salt thereof:

(II)

[Chemical structure showing a polycyclic compound with substituents $R_1O$, $R_2$, $R_3$, $R_4$, $R_5$, $R_6$, $R_7$, $R_8$, $R_9$, $R_{10}$, $R_{11}$, $R_{12}$]

In this formula, $R_1$ is $C_3$-$C_{20}$ cycloalkyl or $C_3$-$C_{20}$ heterocycloalkyl; each of $R_2$, $R_3$, $R_4$, $R_5$, $R_6$, $R_{11}$, and $R_{12}$, independently, is H, $C_1$-$C_{10}$ alkyl, or $OR_a$; each of $R_7$ and $R_{10}$ is H; or $R_7$ and $R_{10}$, taken together, are —O—; $R_8$ is $C_1$-$C_{10}$ alkyl or $COOR_b$; and $R_9$ is H, $OR_c$, or $OC(O)R_c$; in which each of $R_a$, $R_b$, and $R_c$, independently, is H, $C_1$-$C_{10}$ alkyl, $C_3$-$C_{20}$ cycloalkyl, $C_3$-$C_{20}$ heterocycloalkyl, heteroaryl, or aryl.

Referring to formula (II), a subset of the compounds described above are those in which $R_1$ is tetrahydropyranyl substituted with $C_1$-$C_{10}$ alkyl, $C_3$-$C_{20}$ heterocycloalkyl, OR, or COOR; R being H, $C_1$-$C_{10}$ alkyl, $C_3$-$C_{20}$ cycloalkyl, $C_3$-$C_{20}$ heterocycloalkyl, heteroaryl, or aryl; each of $R_2$, $R_3$, $R_4$, $R_5$, $R_6$, $R_{11}$, and $R_{12}$, independently, is H, OH, or $CH_3$ optionally substituted with OH; or $R_8$ is $CH_3$ or COOH.

In still anther aspect, this invention features a method for treating an infection with a coronavirus by administering to a subject in need thereof an effective amount of a compound of formula (III) or a salt thereof:

(III)

[Chemical structure showing an indole-fused polycyclic compound with substituents $R_1$, $R_2$, $R_3$, $R_4$, $R_5$, $R_6$, X and NH]

In this formula, ==== is a single bond or a double bond; X is —O— or —C($R_aR_b$)—; and each of $R_1$, $R_2$, $R_3$, $R_4$, $R_5$, and $R_6$, independently, is H, $C_1$-$C_{10}$ alkyl, $C_3$-$C_{20}$ cycloalkyl, $C_3$-$C_{20}$ heterocycloalkyl, heteroaryl, aryl, $OR_c$, or $COOR_c$; in which each of $R_a$, $R_b$, and $R_c$, independently, is H, $C_1$-$C_{10}$ alkyl, $C_3$-$C_{20}$ cycloalkyl, $C_3$-$C_{20}$ heterocycloalkyl, heteroaryl, aryl, or OC(O)R; R being H, $C_1$-$C_{10}$ alkyl, $C_3$-$C_{20}$ cycloalkyl, $C_3$-$C_{20}$ heterocycloalkyl, heteroaryl, or aryl.

Referring to formula (III), a subset of the compounds described above are those in which ==== is a single bond. In these compounds, X can be —C($R_aR_b$)—; $R_1$, $R_2$, $R_3$, $R_4$, $R_5$, and $R_6$, independently, can be H, OH, $OCH_3$, or $COOCH_3$; and each of $R_a$ and $R_b$, independently, can be H or OC(O)R. Another subset of the compounds described above are those in which ==== is a double bond. In these compounds, X can be —O— and each of $R_1$, $R_2$, $R_3$, $R_4$, $R_5$, and $R_6$, independently, can be H or $COOCH_3$.

In yet another aspect, this invention features a method for treating an infection with a coronavirus (e.g., a severe acute respiratory syndrome virus) by administering to a subject in need thereof an effective amount of compound 3, 4, 6-12, 14, 15, or 17 (structures shown below) or a salt thereof.

In addition, this invention encompasses a pharmaceutical composition that contains an effective amount of at least one of the above-described compounds and a pharmaceutically acceptable carrier.

The compounds that can be used to practice this invention include the compounds themselves, as well as their salts, prodrugs, and solvates, if applicable. A salt, for example, can be formed between an anion and a positively charged group (e.g., amino) on an above-described compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on an above-described compound. Suitable cations include sodium ion, potassium ion, magnesium ion, calcium ion, and an ammonium cation such as tetramethylammonium ion. The above-described compounds also include those salts containing quaternary nitrogen atoms. Examples of prodrugs include esters and other pharmaceutically acceptable derivatives, which, upon administration to a subject, are capable of providing active compounds described above. A solvate refers to a complex formed between an active compound described above and a pharmaceutically acceptable solvent. Examples of pharmaceutically acceptable solvents include water, ethanol, isopropanol, ethyl acetate, acetic acid, and ethanolamine.

Also within the scope of this invention is a composition containing one or more of the above-described compounds for use in treating a coronavirus infection, and the use of such a composition for the manufacture of a medicament for the just-mentioned treatment.

The details of one or more embodiments of the invention are set forth in the description below. Other features, objects, and advantages of the invention will be apparent from the description and from the claims.

DETAILED DESCRIPTION

This invention relates to treating an infection with a coronavirus, such as a severe acute respiratory syndrome virus. Shown below are 35 exemplary compounds (i.e., compounds 1-35) that can be used to practice this invention:

Compound 1
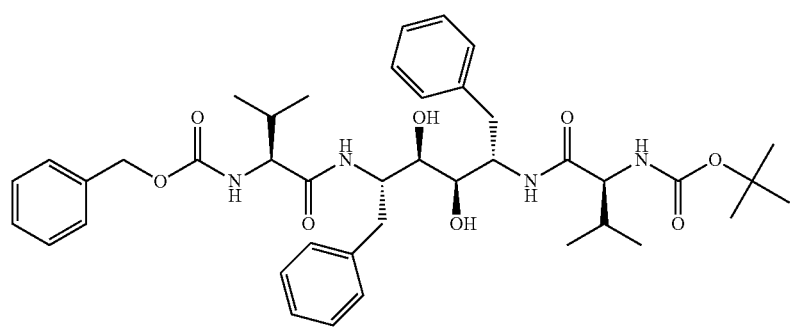
Compound 2
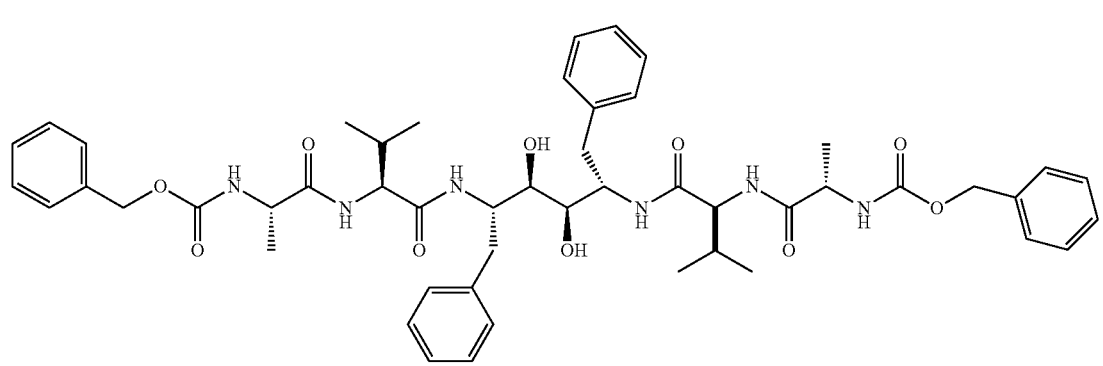
Compound 3
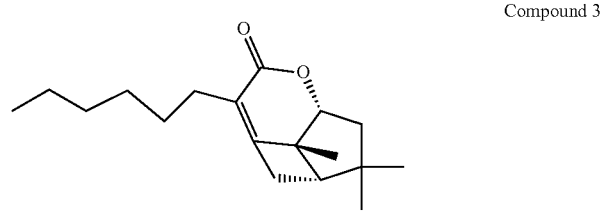
Compound 4
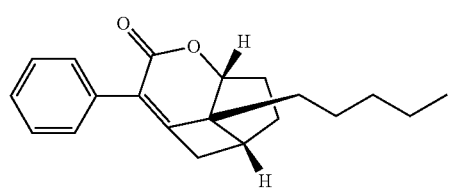
Compound 5
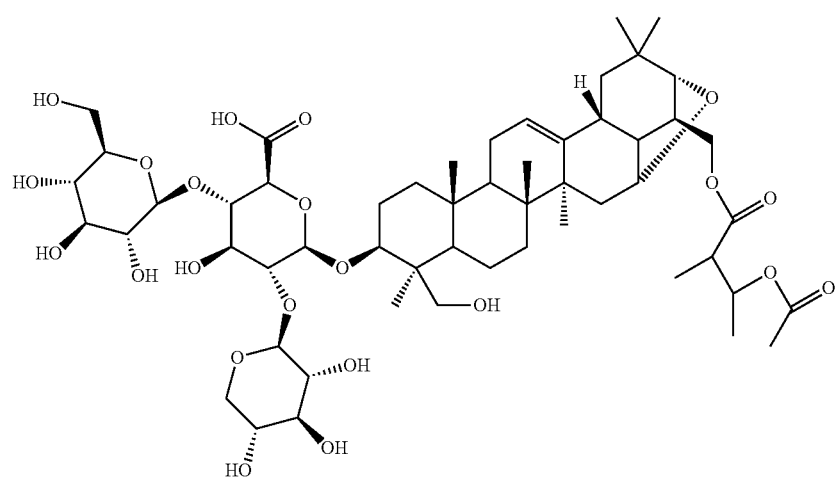
Compound 6
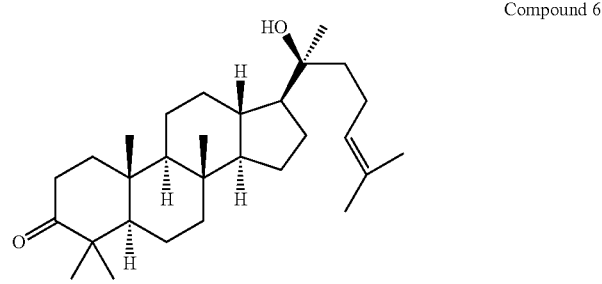
Compound 7
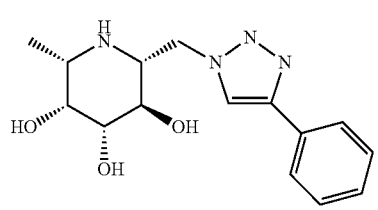

-continued
Compound 8
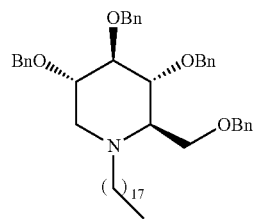
Compound 9
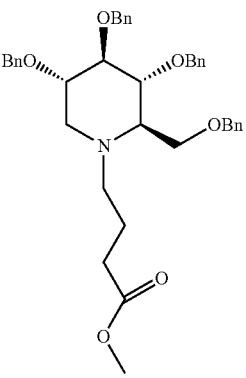
Compound 10
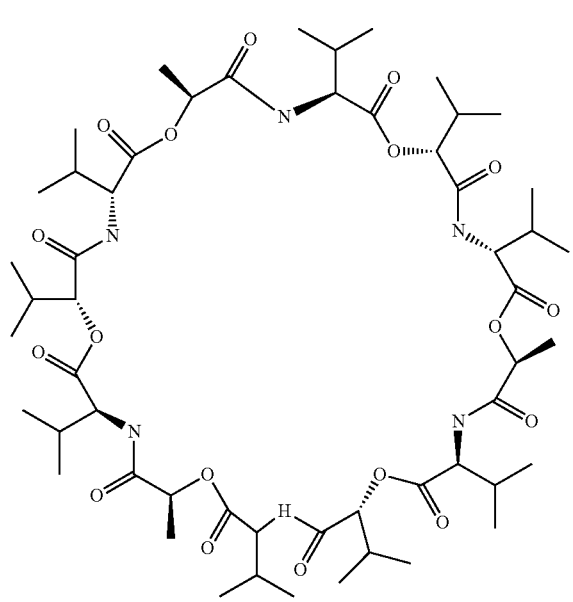
Compound 11
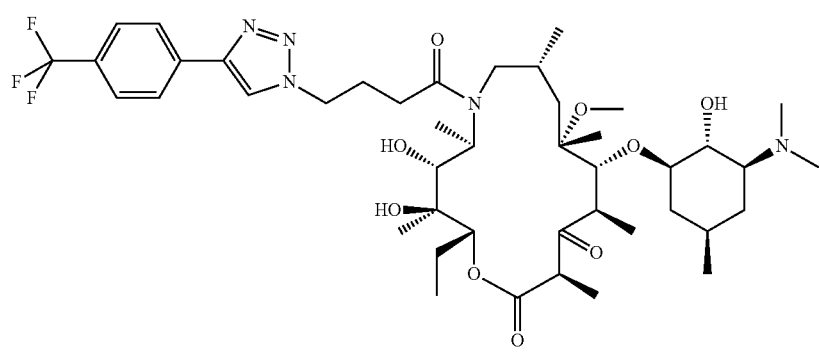

-continued
Compound 12
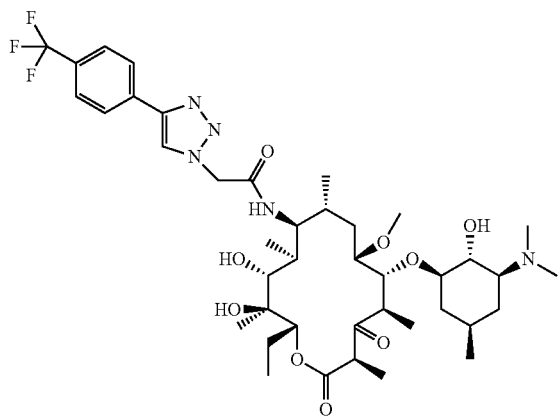
Compound 13
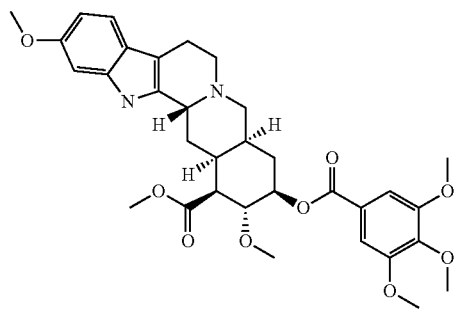
Compound 14
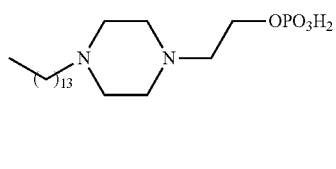
Compound 15
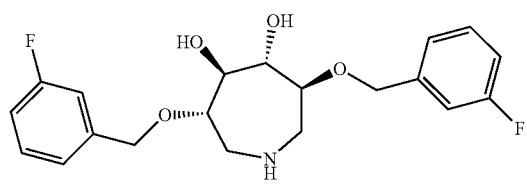
Compound 16
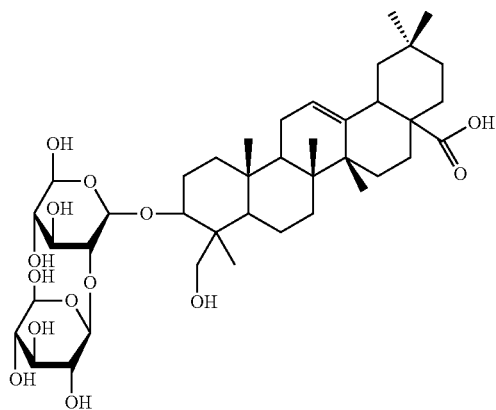
Compound 17
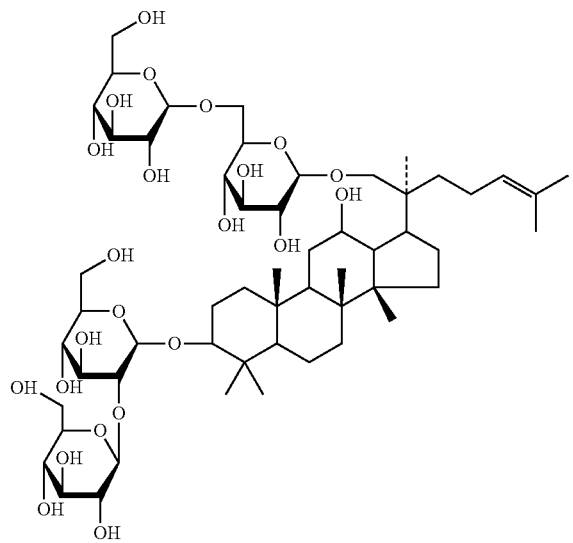
Compound 18
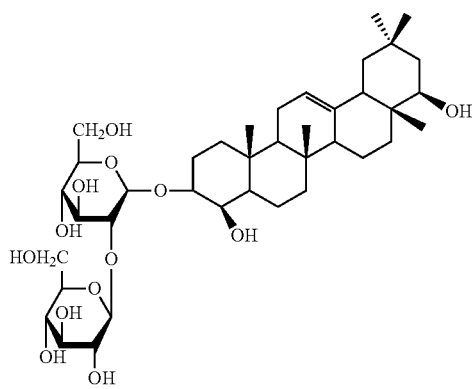
Compound 19
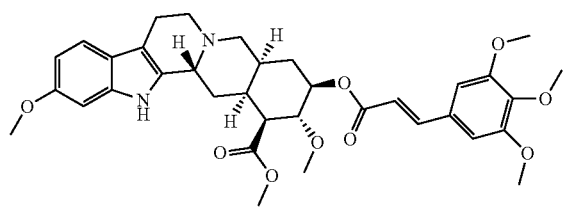

-continued
Compound 20
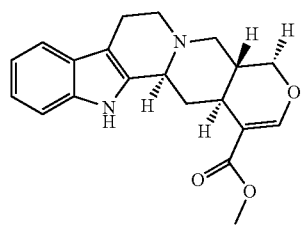
Compound 21
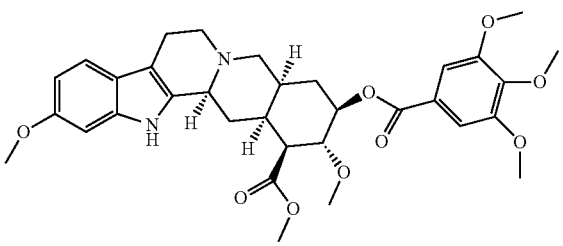
Compound 22
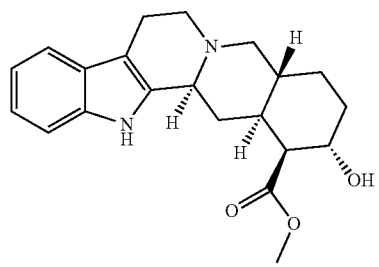
Compound 23
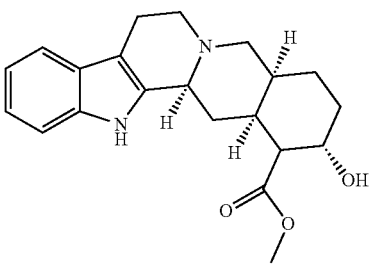
Compound 24
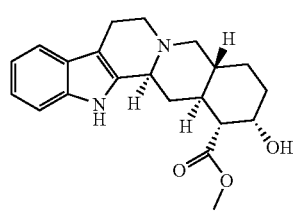
Compound 25
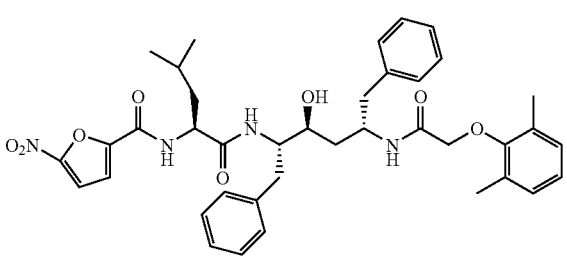
Compound 26
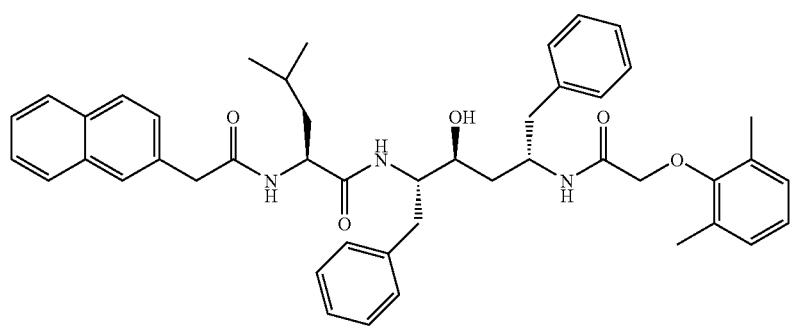
Compound 27
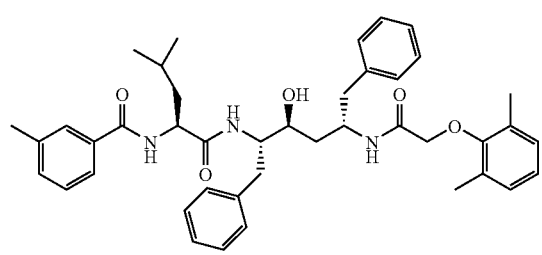
Compound 28
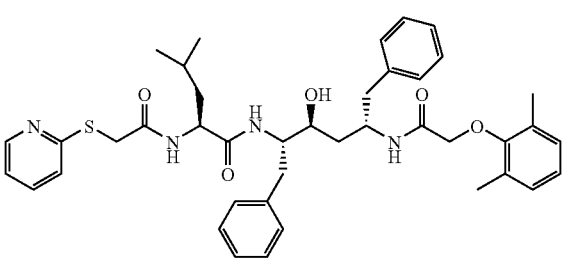

-continued
Compound 29
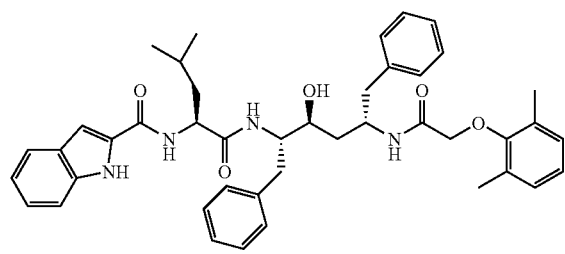
Compound 30
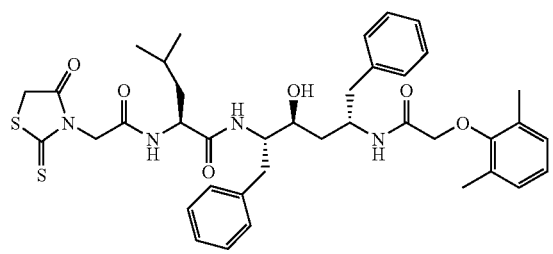
Compound 31
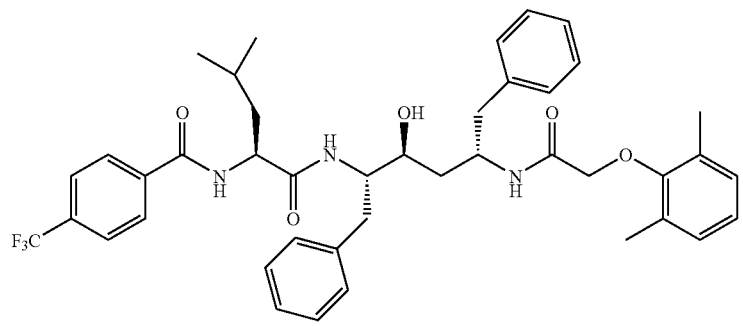
Compound 32
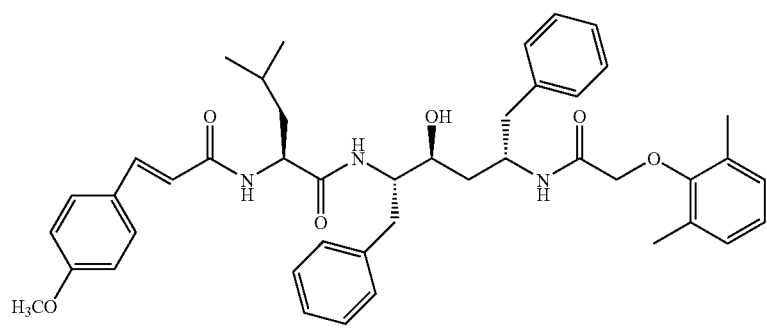
Compound 33
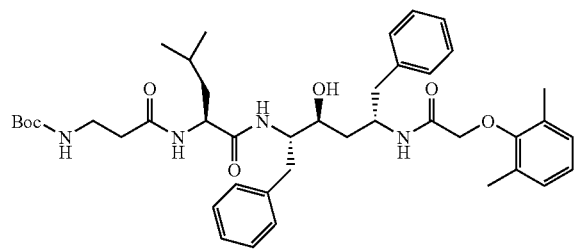
Compound 34
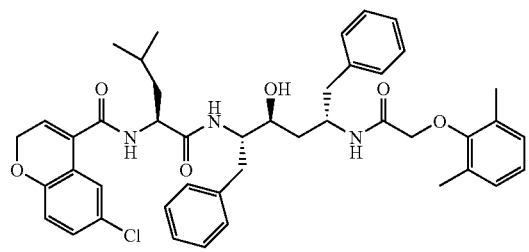
Compound 35
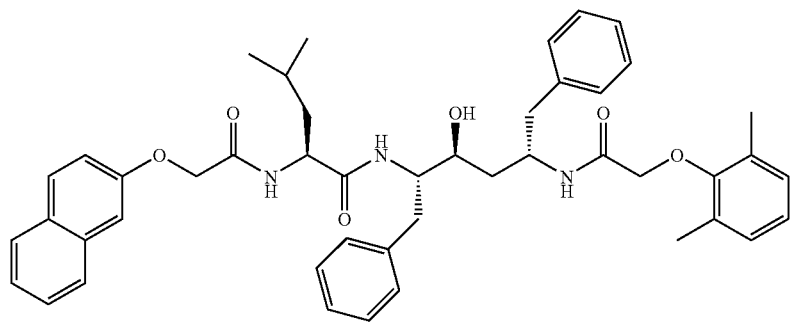

Some of the compounds described above are available from commercial sources, such as Sigma-Aldrich, St. Louis, Mo. All of them can be prepared by known methods. See, e.g., Lee et al., *J. Am. Chem. Soc.,* 1999, 121:1145-1155 and the references cited therein. For instance, compound 25 shown above can be prepared via a series of peptide coupling reactions, which are well known in the art. One of such reactions is described in Example 3 below. Details of preparation of compounds 1, 2, and 26-35 are provided in Examples 1, 2, and 4-13 below. Compounds 3-24 are commercially available. A compound thus synthesized can be purified by a method such as column chromatography, high-pressure liquid chromatography, or recrystallization. Other similar compounds used to practice this invention can be prepared using other suitable starting materials through the above synthetic routes and others known in the art. The methods described above may also include additional steps, either before or after the steps described specifically herein, to add or remove suitable protecting groups in order to ultimately allow synthesis of the compounds described above. In addition, various synthetic steps may be performed in an alternate sequence to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis,* $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

This invention also covers a method of administering an effective amount of one or more of the drug compounds described above to a subject having a coronavirus infection, and optionally, also having a human or feline immunodeficiency virus infection. The drug compounds can be screened for their inhibitory activities against these infections by methods described below or by methods known in the art, such as those described in U.S. Pat. No. 6,803,466 and Lee et al., J. Am. Chem. Soc., 1999, 121:1145-1155.

Further, this invention covers a method of contacting an effective amount of one or more drug compounds described above with a coronavirus protease and optionally, with a human or feline immunodeficiency virus protease or both. The compounds can be screened for their inhibitory activities against one or more of these proteases by methods described below or by methods known in the art, such as those described in U.S. Pat. No. 6,803,466 and Lee et al., J. Am. Chem. Soc., 1999, 121:1145-1155.

Also within the scope of this invention is a pharmaceutical composition containing an effective amount of at least one compound described above and a pharmaceutical acceptable carrier. Regimens for administering such a pharmaceutical composition are well known and, if necessary, can be easily re-established. Effective doses will vary, as recognized by those skilled in the art, depending on the type or degree of the coronaviral infection; the subject's size, weight, age, and sex; the route of administration; the excipient usage; and the possible co-usage with other therapeutic treatment.

To practice the method of the present invention, a composition having one or more of the above-mentioned compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions, and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active above-described compounds can also be administered in the form of suppositories for rectal administration.

A pharmaceutically acceptable carrier is routinely used with one or more active above-mentioned compounds. The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an above-mentioned compound. Examples of other carriers include colloidal silicon oxide, magnesium stearate, cellulose, sodium lauryl sulfate, and D&C Yellow #10.

The compounds described above can be preliminarily screened by in vitro assays for their efficacy against the replication of severe acute respiratory syndrome virus (See Examples 14 and 15 below). Other methods will also be apparent to those of ordinary skill in the art. See, e.g., U.S.

Pat. No. 6,803,466 and Lee et al., J. Am. Chem. Soc., 1999, 121:1145-1155. These compounds can be further screened by in vivo assays.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Compound 1

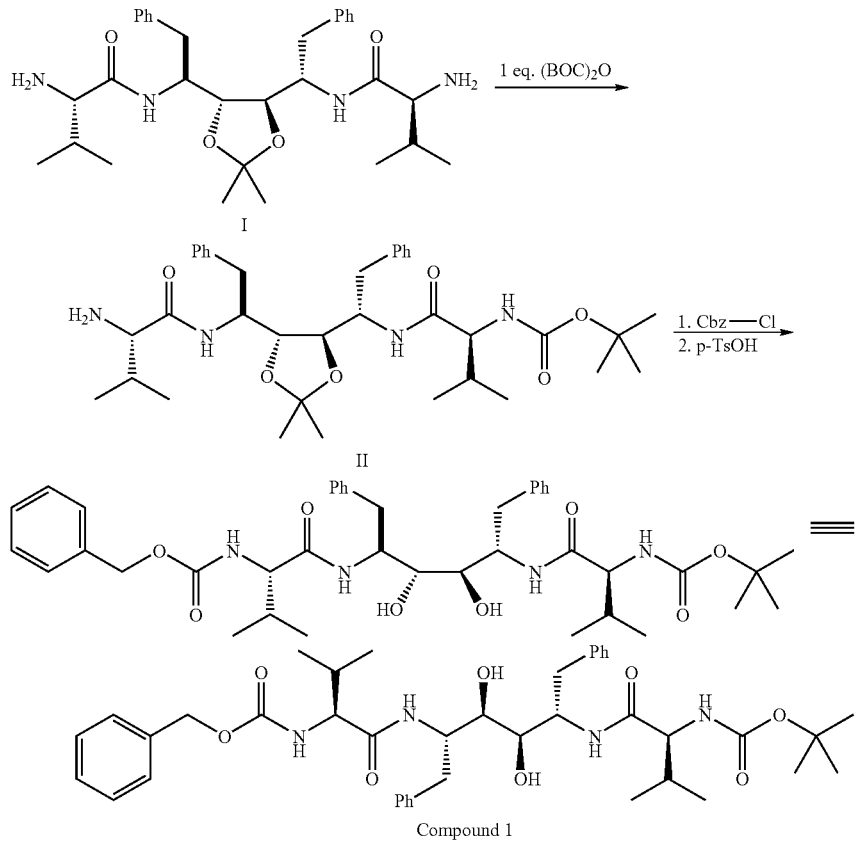

Compound 1

Compound I was prepared according to the method described in Lee et al., *Proc. Natl. Acad. Sci. U.S.A.*, 1998, 95, 939-944.

Compound I (0.6 g, 1.11 mmol) was dissolved in a solution of triethylamine and methanol (10% TEA in MeOH, 5.5 mL). A solution of di-tert-butyl dicarbonate (0.24 g, 1.11 mmol) in methanol (5 mL) was then added dropwise to the above mixture with vigorous stirring. The mixture was stirred at room temperature overnight. The methanol and TEA were removed in vacuo to yield an oily residue. The residue was dissolved in dichloromethane (30 mL) and washed with a solution of a 10% sodium carbonate aqueous solution (2×50 mL). The organic layer was separated, dried over anhydrous $Na_2SO_4$, filtered, and concentrated in vacuo. The oily residue thus obtained was purified by flash column chromatography to give the compound (II) (0.55 g, 78%) as a white solid.

Compound II (0.5 g, 0.78 mmol) was dissolved in dry dichloromethane (10 mL) in the presence of diisopropylethylamine (0.2 mL, 1.56 mmol). After cooling the solution to 0° C., benzyl chloroformate (0.16 g, 0.94 mmol) was added dropwise slowly. After 20 minutes, the reaction was complete (monitored by TLC). The solution was then added to a saturated sodium hydrogen carbonate solution (20 mL) and the mixture was extracted by dichloromethane (3×20 mL). The organic layers were combined, dried with anhydrous $MgSO_4$, and concentrated to afford a crude oil. The crude oil was used for deprotective reaction without purification. Catalytic amounts of p-TsOH were added to a solution of the above crude oil in MeOH (5 mL). The reaction mixture was heated at 60° C. for 24 hours then diluted with EtOAc (20 mL). The organic solution was washed with a saturated $NaHCO_3$ aqueous solution (5 mL), a saturated NaCl aqueous solution (5 mL), dried over anhydrous $MgSO_4$, filtered, and concentrated in vacuo. The oily residue thus obtained was then purified by flash column chromatography to give the compound 1 as a white solid (0.6 g, 75%).

$^1$H NMR (400 MHz, DMSO-d6): 0.71 (6H, m), 0.73 (6H, m), 1.5 (9Hs), 2.17 (1H, se, J=6.7), 2.8-2.9 (3H, m), 3.34 (1H, m), 4.03 (2H, dd, J=8.8, 6.4), 4.10 (1H, qu, J=7.0), 4.27 (1H, s), 4.0-4.20 (1H, m), 4.23-4.32 (1H, m), 6.92-6.96 (1H, br), 7.05-7.34 (12H, m).

$^{13}$CNMR (100 MHz, DMSO-d6, 80° C.), 17.7, 19.6, 19.7, 28.7, 30.4, 30.5, 30.7, 38.3, 45.4, 47.8, 53.0, 60.9, 65.9, 67.1, 72.8, 126.9, 127.6, 128.0, 128.8, 128.9, 129.0, 129.7, 138.3, 172.0, 172.5.

MS (ESI) (M+H$^+$): 733.

EXAMPLE 2

Preparation of Compound 2

Compound 2 was prepared according to the method described in Lee et al., *Proc. Natl. Acad. Sci. U.S.A.*, 1998, 95, 939-944.

$^1$H NMR (400 MHz, DMSO-d6, 80° C.): 0.70 (3H, d, J=2.4), 0.72 (3H, d, J=2.4), 1.21 (3H, d, J=7.0), 1.87 (1H, se, J=6.7), 2.69-2.79 (2H, m), 3.32 (1H, s), 4.03 (1H, dd, J=8.8, 6.4), 4.10 (1H, qu, J=7.0), 4.27 (1H, s), 4.34-4.40 (1H, m), 5.04 (2H, s), 6.92-6.96 (1H, br), 7.05-7.34 (12H, m).

$^{13}$C NMR (100 MHz, DMSO-d6, 80° C.): 17.3, 17.6, 18.7, 29.7, 38.0, 49.9, 50.4, 57.8, 65.1, 72.5, 125.1, 127.0, 127.2, 127.3, 127.8, 128.6, 136.6, 138.4, 155.1, 169.8, 171.6.

HRMS (FAB+) (M+Cs$^+$): 1041.3780.

EXAMPLE 3

Preparation of Compound 25

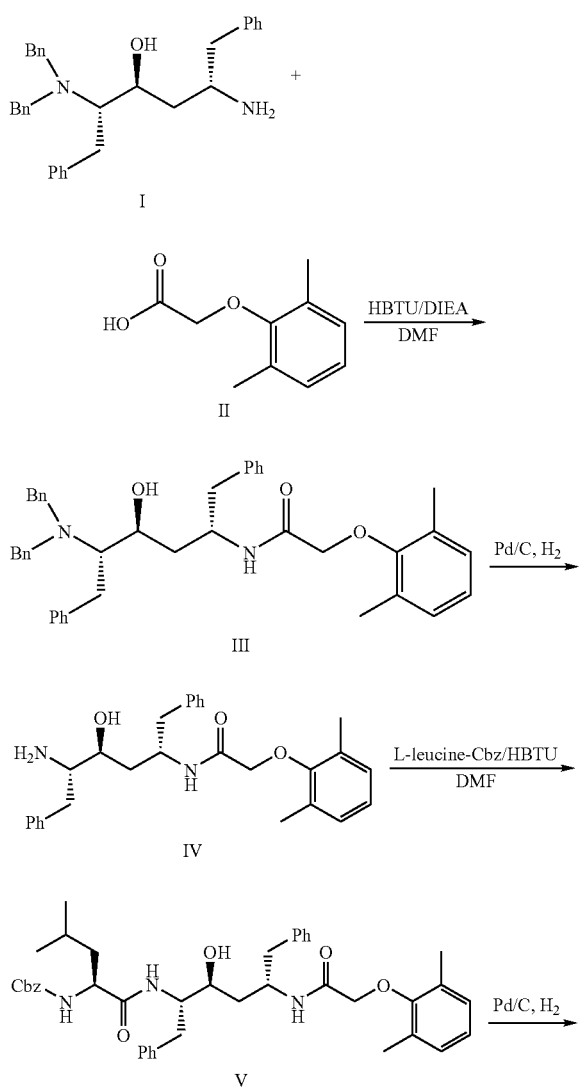

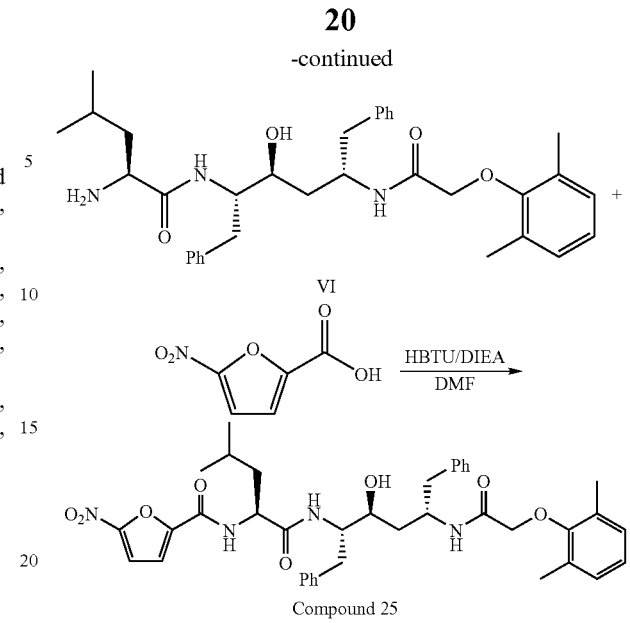

Compounds I and II were respectively prepared according to the methods described in Stuk et al., *J. Org. Chem.* 1994, 59:4040 and Sham et al., *Bioorg. Med. Chem. Lett.* 2002, 12:1185-1187. To a solution of compound I (0.93 g, 2.0 mmol) and compound II (0.38 g, 2.1 mmol) in 20 ml dry DMF was added HBTU (a peptide coupling reagent, 0.80 g, 2.1 mmol) followed by DIEA (0.5 mL, 4.2 mmol) at 20° C. under Ar atmosphere. After stirring for 30 minutes, the reaction mixture was quenched by addition of brine and then extracted with EtOAc. After washing the organic layer with 1 M HCl, a saturated NaHCO$_3$ aqueous solution, and brine, it was dried over anhydrous MgSO$_4$, filtered, and concentrated in vacuo. The crude product thus obtained was purified by flash chromatography to give the compound III in a 90% yield.

Compound III (0.6 g, 0.98 mmol) in EtOAc (40 mL) was stirred under H$_2$ (1 atm) in the presence of 10% Pd/C (200 mg) at 20° C. for 20 hours. The mixture was filtered through celite and then concentrated in vacuo to give compound IV (0.39 g) as a colorless viscous oil, which was used for coupling reaction without purification.

HBTU (0.36 g, 0.96 mmol) and DIEA (0.23 mL, 1.91 mmol) were added to a solution of compound IV (0.39 g, 0.87 mmol) and N-Cbz-L-leucine (0.25 g, 0.96 mmol) in DMF (15 mL). The reaction mixture was stirred for 30 minutes at 20° C. under Ar. After quenching the reaction by addition of brine (45 mL), the mixture was extracted with EtOAc (4×30 mL). The organic layers were combined and washed sequentially with 1 M HCl (10 mL), a saturated NaHCO$_3$ aqueous solution (10 mL), and a saturated NaCl aqueous solution (10 mL). The organic phase was then dried over anhydrous MgSO$_4$, filtered, and concentrated in vacuo. The crude product thus obtained was purified by flash chromatography to give compound V (0.53 g, 78% two steps) as a white solid.

Compound V (0.5 g, 0.728 mmol) in EtOAc (40 mL) was stirred under H$_2$ (1 atm) in the presence of 10% Pd/C (200 mg) at 20° C. for 20 hours. The mixture was filtered through celite and then concentrated in vacuo. The crude product thus obtained was purified by flash chromatography to give compound VI (0.37 g, 92%) as a white solid.

HBTU (0.15 g, 0.40 mmol) and DIEA (0.1 mL, 0.80 mmol) were added to a solution of compound VI (0.2 g, 0.36 mmol) and 5-nitro-furan-2-carboxylic acid (62.8 mg, 0.40 mmol) in DMF (15 mL). After stirring for 30 minutes at 20° C. under Ar, the reaction was quenched by addition of brine (45 mL) and the mixture was extracted with EtOAc (4×30 mL). The organic layers were combined and washed sequentially with 1 M HCl (10 mL), a saturated NaHCO$_3$ aqueous solution (10 mL), and a saturated NaCl aqueous solution (10 mL). The organic phase was then dried over anhydrous MgSO$_4$, filtered, and concentrated in vacuo. The crude product thus obtained was purified by flash chromatography to give compound 25 (0.23 g, 90%) as a white solid.
LC-MS (M+H$^+$): 699.

EXAMPLE 4

Preparation of Compound 26

Compound 26 was prepared in a manner similar to that described in Example 3.
LC-MS (M+H$^+$): 747.

EXAMPLE 5

Preparation of Compound 27

Compound 27 was prepared in a manner similar to that described in Example 3.
LC-MS (M+H$^+$): 678.

EXAMPLE 6

Preparation of Compound 28

Compound 28 was prepared in a manner similar to that described in Example 3.
LC-MS (M+H$^+$): 711.

EXAMPLE 7

Preparation of Compound 29

Compound 29 was prepared in a manner similar to that described in Example 3.
LC-MS (M+H$^+$): 703.

EXAMPLE 8

Preparation of Compound 30

Compound 30 was prepared in a manner similar to that described in Example 3.
LC-MS (M+H$^+$): 733.

EXAMPLE 9

Preparation of Compound 31

Compound 31 was prepared in a manner similar to that described in Example 3.
LC-MS (M+H$^+$): 732.

EXAMPLE 10

Preparation of Compound 32

Compound 32 was prepared in a manner similar to that described in Example 3.
LC-MS (M+H$^+$): 720.

EXAMPLE 11

Preparation of Compound 33

Compound 33 was prepared in a manner similar to that described in Example 3.
LC-MS (M+H$^+$): 731.

EXAMPLE 12

Preparation of Compound 34

Compound 34 was prepared in a manner similar to that described in Example 3.
LC-MS (M+H$^+$): 752.

EXAMPLE 13

Preparation of Compound 35

Compound 35 was prepared in a manner similar to that described in Example 3.
LC-MS (M+H$^+$): 744.

EXAMPLE 14

Screening Assays

Compounds 1-35 were initially screened for their inhibitory activity against severe acute respiratory syndrome virus by observing cytopathogenic effect (CPE). The assay procedures are as follows: Vero E6 cells (2×104/well) were cultured in a 96-well plate in Dulbecco's Modified Eagle's Medium (DMEM) supplemented with 10% fetal bovine serum (FBS). The culture medium was removed after one-day incubation when the cells reached 80-90% confluence. Solutions of 100 μL of DMEM with 2% FBS containing 10 μL of a test compound were placed in wells (in triplicate). Cells in DMEM with 2% FBS were used as a CPE-positive control (also in triplicate). All of the cells were then incubated in a CO$_2$ incubator at 37° C. for 2 hours, followed by inoculation with severe acute respiratory syndrome virus (H.K.) at a dose of 100 TCID$_{50}$/well. The cytopathic morphology of the cells was examined using an inverted microscope 72 hours after the infection.

The inhibitory activity of the test compounds was confirmed by using immunofluorescence enzyme-linked immunosorbent assay (ELISA), immunofluorescence assay (IFA), western blot analysis (WBA), flow cytometry analysis (FCA), and 3CL-protease inhibition assay. A detailed description of these assays are provided below:

Immunofluorescence Enzyme-Linked Immunosorbent Assay

After incubating Vero E6 cells with severe acute respiratory syndrome virus and a test compound, cells were rinsed with phosphate-buffered saline (PBS), fixed in a solution containing ice methanol:acetone=1:1 for 3 minutes at room temperature, and rinsed three times with PBS. The cells were then blocked with 3% skimmed milk in PBS for 30 minutes at room temperature and incubated for 1 hour at 37° C. with 1:2,000 diluted monoclonal antibody (ascetic fluid) to the spike protein of severe acute respiratory syndrome virus. All samples were washed with PBS-T buffer three times and PBS buffer twice at room temperature, followed by a 30-minute incubation with HRP-labeled goat anti-mouse IgG for 30 minutes at room temperature. Plates were rinsed with PBS containing 0.05% Tween 20 between incubations. A substrate solution containing O-phenylenediamine dihydrochloride, citrate buffer (pH 5.0), and hydrogen peroxide was added to each well. The plates were then covered and gently shaken at room temperature for 10 minutes. After the reaction was stopped by addition of 3N sulfuric acid, the fluorescence intensity of each plate was measured immediately at 492 nm. The $EC_{50}$ value for each agent was extrapolated from the linear regression plot of agent concentration versus $OD_{492}$.

Immunofluorescence Assay

Infected or control cells were rinsed with PBS and re-suspended to a final concentration of $1\times10^6$ cells/mL. Slides were prepared for IFA by spotting wells with $2\times10^4$ cells for each test compound concentration or for each control. The slides were then dried, fixed in an ice methanol:acetone=1:1 solution for 3 minutes, rinsed and stored at $-20°$ C. before staining for IFA. Daudi cells were rehydrated and then blocked with 3% skimmed milk in PBS for 30 minutes at room temperature. Vero E6 cells were rehydrated, blocked, and permeabilized in PBS containing 0.1% saponin and 1% FBS. All other cells were rehydrated, blocked, and permeabilized in PBS containing 5% FBS, 4% normal goat serum and 0.5% DMSO for 30 minutes. The cells were then incubated in a hydration chamber at 37° C. for 1 hour with a primary antibody diluted in a blocking solution. Following a rinse with PBS, cells were incubated at 37° C. for 1 hour with 3 g/mL FITC-conjugated goat anti-mouse IgG+IgM secondary antibody (Jackson ImmunResearch, West Grove, Pa.). After rinsing with PBS again, cells were stained with 0.1% Evans blue dye (Fisher, Fair Lawn, N.J.) in PBS for 5 minutes. Slides were rinsed to remove any excess contrast dye and cover slides were mounted using a solution of 50% glycerol in PBS. The cells were observed under a Nikon (Nikon, Melville, N.Y.) fluorescence microscope at a magnification of 400×. For each test compound concentration, 500 cells were counted and the percentage of antigen-positive cells was calculated. The concentration required to inhibit 50% virus replication ($EC_{50}$) was determined.

Western Blot Analysis

Severe acute respiratory syndrome virus infected Vero E6 cells were treated with a test compound at various concentrations for 24 or 48 hours and then lysed in a lysis buffer for 3 minutes. The cell debris was spun down and all cell lysates were harvested for electrophoresis and western blotting assay with SDS-PAGE and a Hybond-C Extra membrane (Amersham Biosciences, Piscataway, N.J.). The resulting membrane was blocked in 3% skimmed milk in PBS for 30 minutes at room temperature, and then treated with either 1:5,000 diluted anti-spike protein monoclonal ascetic fluid or 1:2,000 diluted mouse anti-actin Ab (Chemicon MAb 1501) for 1 hour at room temperature. The membrane was rinsed using two batches of PBS-T buffer and then washed once for 15 minutes and twice for 5 minutes with PBS at room temperature. The membrane was then treated with 1:2,000 diluted HRP-labeled goat anti-mouse IgG for 30 minutes and for 1 hour. The membrane was washed as above and a mixed ECL detection reagent was added to the protein side of the membrane. The blot was placed in a film cassette with the protein side up to observe the level of protein expression.

Flow Cytometry Analysis

Vero E6 cells were rinsed and blocked with 5% FBS and 4% goat serum in PBS. Severe acute respiratory syndrome virus infected cells were trypsinized with 0.05% trypsin-EDTA medium. About $1-5\times10^5$ cells were distributed to each well of a round-bottom ELISA plate or to each 1.5 mL microtube containing cell culture medium. The suspension was centrifuged and the cells were rinsed with PBS and resuspended. 100 μL of CYTOFIX/CYTOPERM solution was added to each well or microtube. The cells were fixed and permeabilized in 2 mL methanol for 20 minutes at 4° C. The cells were then blocked in PBS containing 5% FBS, 4% serum, and 0.5% DMSO for 30 minutes at 37° C. The cells were incubated with 20 mL of primary antibody diluted in a blocking solution for 1 hour at 37° C., then rinsed twice with 4 mL of the blocking solution and pelleted by centrifugation at 1000×g for 5 minutes. After the second rinse, 0.5 mL of 3 g/mL FITC conjugated goat anti-mouse IgG+IgM (Jackson ImmunoResearch, West Grove, Pa.) was added, followed by incubating the cells for 1 hour at 37° C. The cells were then rinsed twice with PBS and pelleted by centrifugation before being resuspended.

Flow cytometry data was acquired using a Becton-Dickenson FacsCalibur instrument and analyzed by a Win-MDI 2.7 data analysis program (Scripps Research Institute, La Jolla, Calif.). The resulting dot plots were gated to remove non-specific and background staining and an M1 bar was set so that less than 1% of the cells in the negative control were included in the determination of the percentage of the positive cells. The $EC_{50}$ value for each test compound was extrapolated using a plot drawn based on the compound concentration versus the percentage of antigen positive cells.

3CL-Protease Inhibition Assay

The gene encoding the main protease of severe acute respiratory syndrome virus was cloned from the viral whole genome by using polymerase chain reaction with the forward primer as 5'-GGTATTGAGGGTCGCA-GTGGTTTTAGG-3' and reverse primer as 5'-AGAGGAGAGTTAGAGCCT-TATTGG-AAGGTAACACC-3'. The PCR products flanked by the two primers were subcloned into the pET32Xa/Lic vector. The FXa cleavage site (IEGR) and the complementary sequences to the sticky ends of the linear vector pET-32Xa/LIC were included in these primers. The recombinant protease plasmid was then used to transform *E. coli* JM109 competent cells that were streaked on a Luria-Bertani (LB) agar plate containing 100 μg/mL ampicillin. The correct construct was subsequently transformed into *E. coli* BL21 for expression of the His-tagged protein, which was then digested with FXa protease to remove the tag. The structure of the purified protein was confirmed by N-terminal sequencing and mass spectrometry. The enzyme concentration used in all experiments was determined from the absorbance at 280 nm.

All kinetic measurements were performed in 20 mM Bis-Tris (pH 7.0) at 25° C. Enhanced fluorescence due to cleavage of the fluorogenic substrate peptide (Dabcyl-KTSAVLQ-SG-FRKME-Edans) was monitored at 538 nm with excitation at 355 nm using a fluorescence plate reader (Fluoroskan Ascent from ThermoLabsystems, Sweden).

Compound 1-35 were tested using the above-described assays. Unexpectedly, all of them showed low $EC_{50}$ values, i.e., between 0.85 μM and 100 μM.

EXAMPLE 15

Cytotoxicity Assay

Vero E6 cells were grown in a humidified 5% $CO_2$ incubator at 37° C. in DMEM supplemented with L-glutamine, non-essential amino acids, and 10% FBS in 75 $cm^3$ flasks. The cells were then seeded at $7\times10^4$ cells $ml^{-1}$ onto a 96-well plate and left overnight.

Living cell populations was determined using Cell Titer 96 non-Radioactive Cell Proliferation Assay Kits (Promega, Madison, Wis.). The kits measure the amount of Formazan produced by metabolic conversion of Owen's reagent, 3-(4, 5-dimethylthiazol-2-yl)-5-(3-carboxymethoxyphenyl)-2-(4-sulfo-phenyl)-2H-tetrazolium, inner salt (MTS), by a dehydrogenase present in the mitochondria of metabolically active cells and is directly proportional to the number of living cells. Briefly, after the incubations with a test compound at various concentrations for 2 days, the culture medium was replaced with MTS/phenazine methosulfate in DMEM. After a 2-hour incubation at 37° C., the absorbance was measured with a plate reader at 490 nm. Data were expressed as the percentage of control cells cultured in the absence of any test compounds (as 100%).

Cytotoxicity of compounds 1-15 were tested. Unexpectedly, none of them exhibited inhibitory effect on cell growth at a concentration equal to the $EC_{50}$ concentration against severe acute respiratory syndrome virus. Further, 10 of the test compounds exhibited no inhibitory effect on cell growth at a concentration four times as high as the $EC_{50}$ concentration against severe acute respiratory syndrome virus.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating a subject suffering from a viral infection caused by a severe acute respiratory syndrome virus, comprising administering to the subject an effective amount of a composition consisting of a pharmaceutically acceptable carrier and a compound of formula (I):

wherein
$R_1$ is H, $C_1$-$C_{10}$ alkyl, $C_3$-$C_{20}$ cycloalkyl, $C_3$-$C_{20}$ heterocycloalkyl, heteroaryl, aryl, or $OR_a$;
each of $R_2$, $R_3$, $R_4$ and $R_{10}$, independently, is H, $C_1$-$C_{10}$ alkyl, $C_3$-$C_{20}$ cycloalkyl, $C_3$-$C_{20}$ heterocycloalkyl, heteroaryl, or aryl;
each of $R_5$ and $R_{11}$, independently, is alkyl substituted with aryl;
each of $R_6$, $R_7$, $R_8$, and $R_9$, independently, is H, $C_1$-$C_{10}$ alkyl, $C_3$-$C_{20}$ cycloalkyl, $C_3$-$C_{20}$ heterocycloalkyl, heteroaryl, aryl, or $OR_b$; and
$R_{12}$ is $C_1$-$C_{10}$ alkyl substituted with $OR_c$, $NHC(O)R_c$, or $NHC(O)OR_c$;
in which each of $R_a$, $R_b$, and $R_c$, independently, is H, $C_1$-$C_{10}$ alkyl, $C_3$-$C_{20}$ cycloalkyl, $C_3$-$C_{20}$ heterocycloalkyl, heteroaryl, or aryl;
or a salt thereof.

2. The method of claim 1, wherein $R_1$ is $C_1$-$C_{10}$ alkyl, $C_3$-$C_{20}$ heterocycloalkyl, heteroaryl, aryl, or $OR_a$; each of $R_2$, $R_3$, $R_4$ and $R_{10}$, independently, is H or $C_1$-$C_{10}$ alkyl; and each of $R_6$, $R_7$, $R_8$, and $R_9$, independently, is H or $OR_b$.

3. The method of claim 2, wherein each of $R_5$ and $R_{11}$ is alkyl substituted with phenyl.

4. The method of claim 3, wherein $R_2$ is isopropyl.

5. The method of claim 4, wherein each of $R_6$, $R_7$, $R_8$, and $R_9$, independently, is H or OH.

6. The method of claim 5, wherein $R_1$ is $C_3$-$C_{20}$ heterocycloalkyl, heteroaryl, aryl, $OR_a$, or $C_1$-$C_{10}$ alkyl substituted with a substituent selected from the group consisting of $C_3$-$C_{20}$ cycloalkyl, $C_3$-$C_{20}$ heterocycloalkyl, heteroaryl, aryl, OR, SR, and NHC(O)OR; R being H, $C_1$-$C_{10}$ alkyl, $C_3$-$C_{20}$ cycloalkyl, $C_3$-$C_{20}$ heterocycloalkyl, heteroaryl, or aryl.

7. The method of claim 6, wherein the compound is

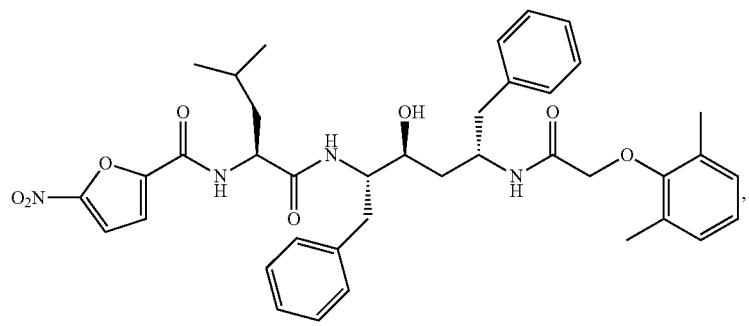
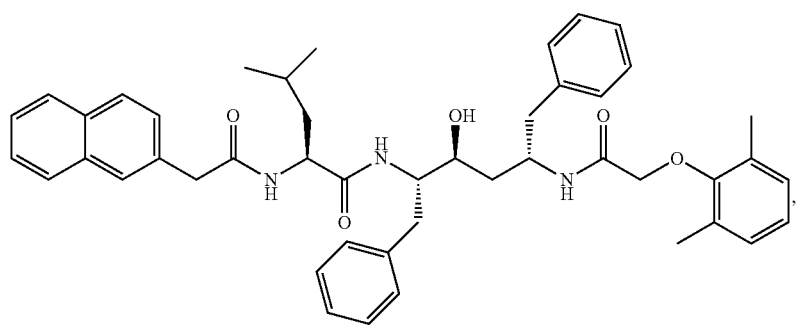
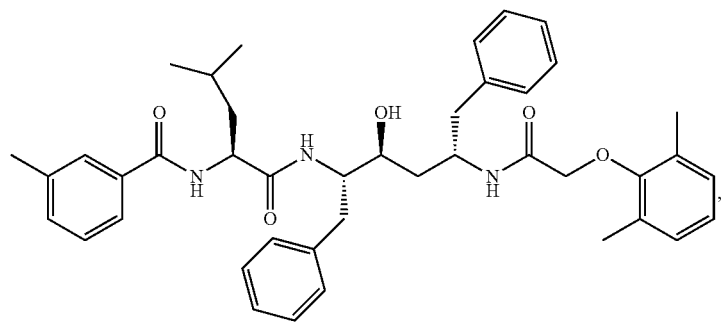
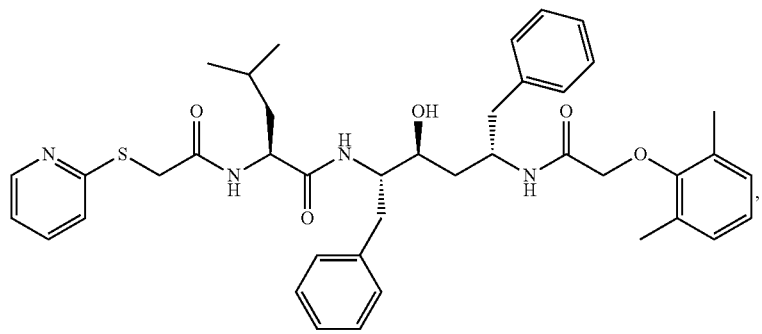

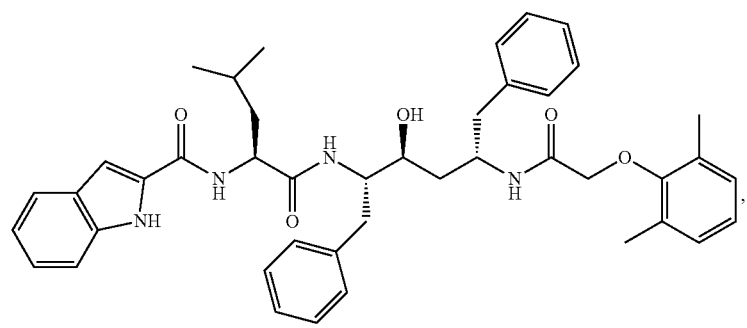
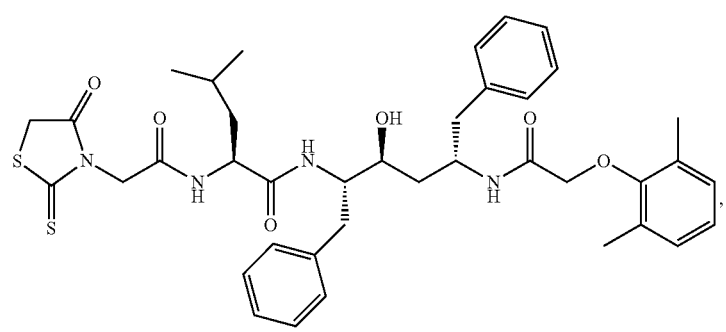
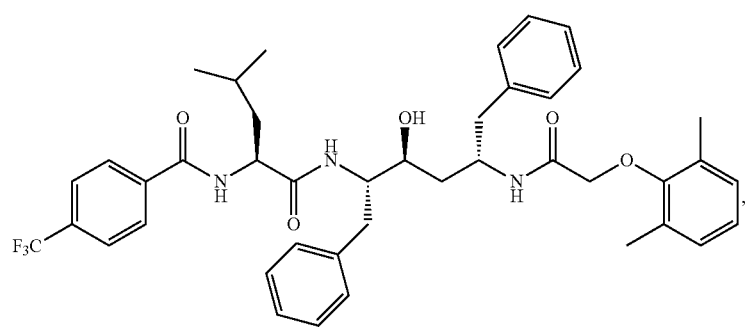
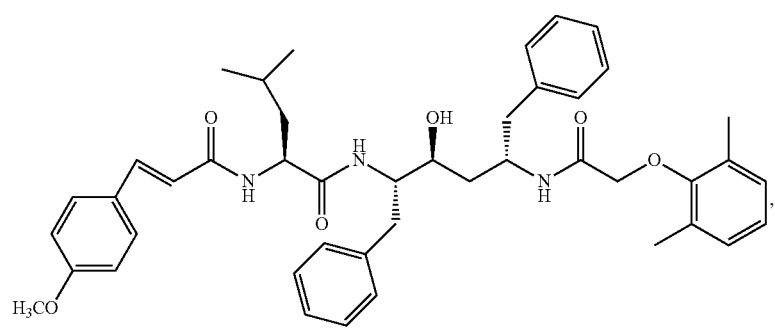

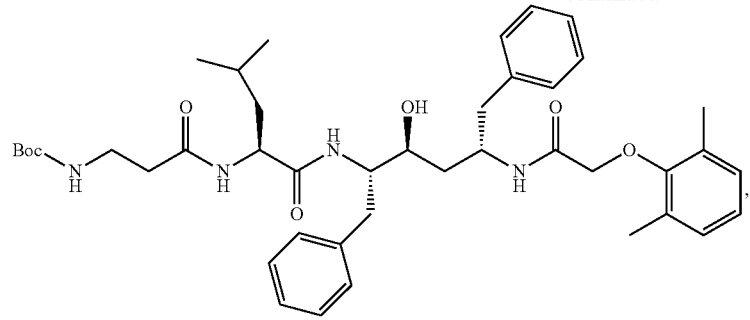
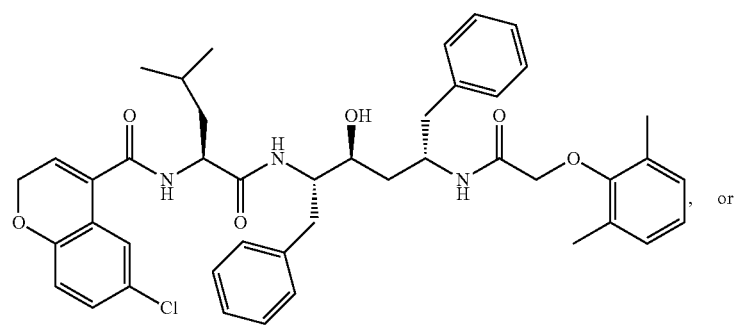
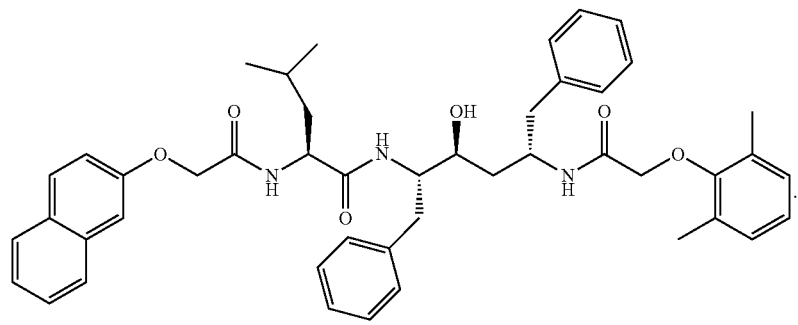
8. The method of claim 7, wherein the compound is
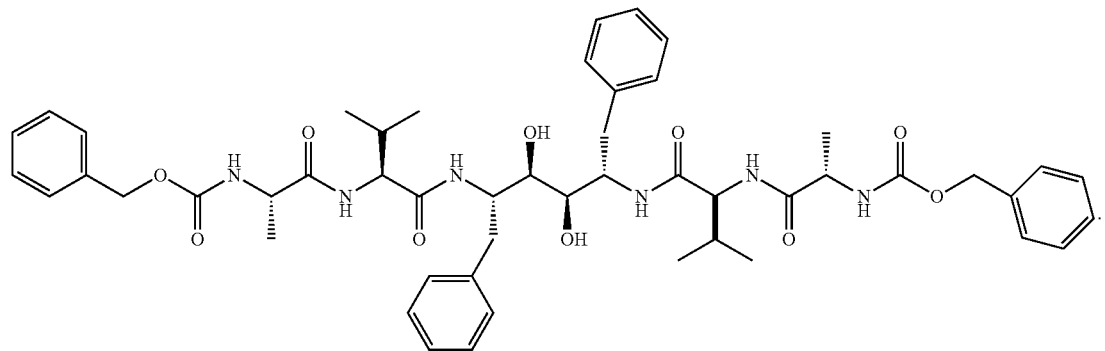 [SMILES: CC(C)[C@H](NC(=O)[C@H](C)NC(=O)OCc1ccccc1)C(=O)N[C@@H](Cc1ccccc1)[C@@H](O)[C@H](O)[C@H](Cc1ccccc1)NC(=O)[C@@H](NC(=O)[C@H](C)NC(=O)OCc1ccccc1)C(C)C ; "."]

9. The method of claim 1, wherein the subject further suffers from an infection caused by a human immunodeficiency virus.
10. The method of claim 9, wherein the compound is
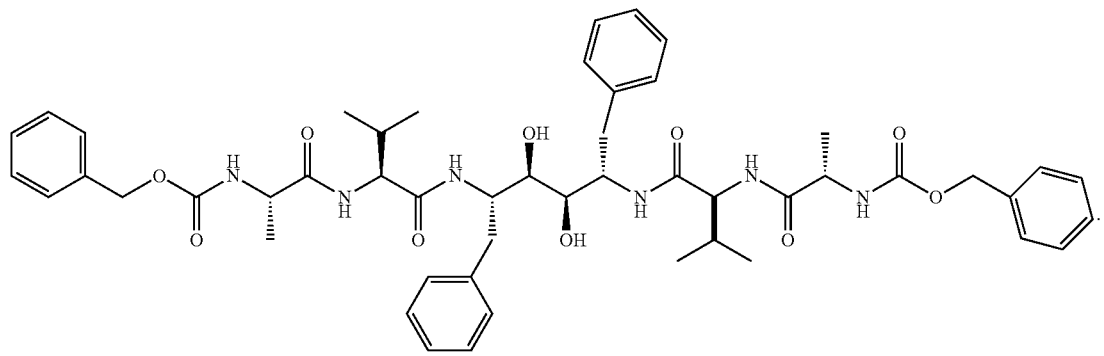 [SMILES: CC(C)[C@H](NC(=O)[C@H](C)NC(=O)OCc1ccccc1)C(=O)N[C@@H](Cc1ccccc1)[C@@H](O)[C@H](O)[C@H](Cc1ccccc1)NC(=O)[C@@H](NC(=O)[C@H](C)NC(=O)OCc1ccccc1)C(C)C ; "."]
11. The method of claim 1, wherein the subject further suffers from an infection caused by a feline immunodeficiency virus.
12. The method of claim 11, wherein the compound is
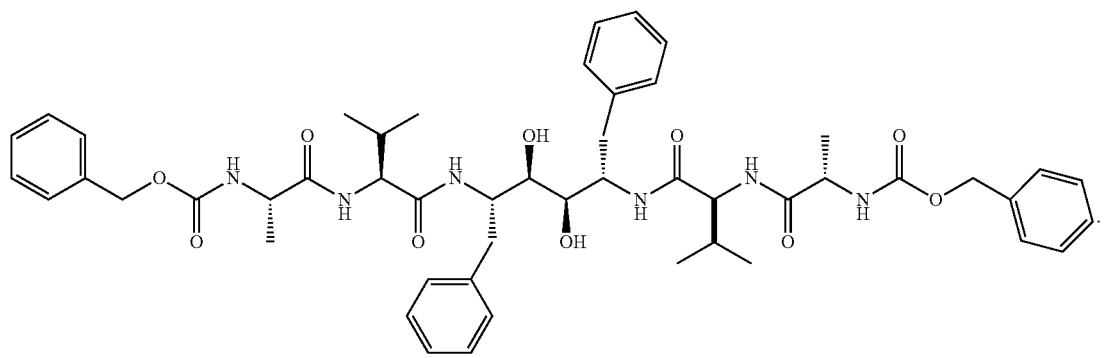 [SMILES: CC(C)[C@H](NC(=O)[C@H](C)NC(=O)OCc1ccccc1)C(=O)N[C@@H](Cc1ccccc1)[C@@H](O)[C@H](O)[C@H](Cc1ccccc1)NC(=O)[C@@H](NC(=O)[C@H](C)NC(=O)OCc1ccccc1)C(C)C ; "."]
* * * * *